(12) United States Patent
Sasikumar et al.

(10) Patent No.: US 11,191,597 B1
(45) Date of Patent: Dec. 7, 2021

(54) ROBOTIC MEDICAL ASSISTANT VEHICLE AND INTERFACE

(71) Applicants: Arya Sasikumar, Dublin, CA (US);
Sasikumar Allidurai, Dublin, CA (US);
Shreya Sripada, Dublin, CA (US);
Nandana Abburi, Dublin, CA (US);
Arunan Elamaran, Dublin, CA (US);
Arjun Reddy, Dublin, CA (US);
Rodrigo Colin, Dublin, CA (US);
Iniyan Sasikumar, Dublin, CA (US)

(72) Inventors: Arya Sasikumar, Dublin, CA (US);
Sasikumar Allidurai, Dublin, CA (US);
Shreya Sripada, Dublin, CA (US);
Nandana Abburi, Dublin, CA (US);
Arunan Elamaran, Dublin, CA (US);
Arjun Reddy, Dublin, CA (US);
Rodrigo Colin, Dublin, CA (US);
Iniyan Sasikumar, Dublin, CA (US)

( * ) Notice: Subject to any disclaimer, the term of this patent is extended or adjusted under 35 U.S.C. 154(b) by 0 days.

(21) Appl. No.: 17/217,847

(22) Filed: Mar. 30, 2021

Related U.S. Application Data

(60) Provisional application No. 63/016,801, filed on Apr. 28, 2020.

(51) Int. Cl.
| | | |
|---|---|---|
| A61B 34/00 | (2016.01) |
| A61B 34/30 | (2016.01) |
| A61B 5/024 | (2006.01) |
| A61B 5/022 | (2006.01) |
| A61B 5/01 | (2006.01) |
| A61B 5/00 | (2006.01) |
| A61B 10/00 | (2006.01) |
| A61B 5/145 | (2006.01) |
| A01G 5/04 | (2006.01) |
| A61G 5/04 | (2013.01) |

(52) U.S. Cl.
CPC ............ *A61B 34/25* (2016.02); *A61B 5/0004* (2013.01); *A61B 5/01* (2013.01); *A61B 5/024* (2013.01); *A61B 5/02241* (2013.01); *A61B 5/14542* (2013.01); *A61B 5/6898* (2013.01); *A61B 10/0051* (2013.01); *A61B 34/30* (2016.02); *A61B 34/70* (2016.02); *A01G 5/04* (2013.01); *A61B 2560/0214* (2013.01); *A61G 5/04* (2013.01)

(58) Field of Classification Search
CPC ....... A61B 5/01; A61B 5/024; A61B 5/14542; A61B 10/0051; A61B 34/30; A61G 5/04
See application file for complete search history.

(56) References Cited

U.S. PATENT DOCUMENTS

| | | | | |
|---|---|---|---|---|
| 5,033,489 A | * | 7/1991 | Ferre | B60S 3/008 134/57 R |
| 10,315,585 B2 | * | 6/2019 | Minn | F16B 2/065 |
| 10,967,368 B1 | * | 4/2021 | Moore | B01L 1/52 |

(Continued)

*Primary Examiner* — Daniel L Cerioni
*Assistant Examiner* — Raymond P Dulman
(74) *Attorney, Agent, or Firm* — Plager Schack LLP; Mark H. Plager; Stephen Hallberg (57) ABSTRACT

A robotic medical assistant vehicle and interface (R-MAVI) is disclosed. The robotic medical assistant vehicle and interface helps contain viruses by reducing human interaction. The robotic medical assistant vehicle and interface combines robotics with medicine to achieve the safest and most efficient reception, transportation and initial assessment of a patient.

9 Claims, 8 Drawing Sheets

(56) References Cited

U.S. PATENT DOCUMENTS

| | | | | |
|---|---|---|---|---|
| 11,008,629 B1* | 5/2021 | Tanner | .................... | C12Q 1/701 |
| 2005/0214159 A1* | 9/2005 | Schwei | ..................... | A61L 2/18 |
| | | | | 422/28 |
| 2006/0107486 A1* | 5/2006 | Andre | .................... | B08B 15/02 |
| | | | | 15/302 |
| 2012/0068848 A1* | 3/2012 | Campbell | ............... | G16H 50/20 |
| | | | | 340/573.1 |
| 2015/0216746 A1* | 8/2015 | Dirauf | ................... | A61G 7/012 |
| | | | | 701/25 |
| 2015/0296990 A1* | 10/2015 | Malik | ..................... | A61G 5/10 |
| | | | | 280/47.38 |
| 2017/0266069 A1* | 9/2017 | Lozano | ................... | A61G 5/04 |
| 2018/0034308 A1* | 2/2018 | Burkhart | ................ | H02J 7/342 |
| 2018/0164829 A1* | 6/2018 | Oshima | ................. | G05D 1/024 |
| 2019/0049977 A1* | 2/2019 | Dean | .................... | G05D 1/0278 |
| 2020/0306395 A1* | 11/2020 | Gardiner | ................ | A61L 2/22 |
| 2021/0089037 A1* | 3/2021 | Fukuoka | ............... | G01C 21/20 |
| 2021/0145363 A1* | 5/2021 | Cho | .................... | A61B 5/6838 |
| 2021/0145665 A1* | 5/2021 | Coulter | ................ | B60L 15/025 |

\* cited by examiner

ROBOTIC MEDICAL ASSISTANT VEHICLE AND INTERFACE

CLAIM OF BENEFIT TO PRIOR APPLICATION

This application claims benefit to U.S. Provisional Patent Application 63/016,801, entitled "ROBOTIC MEDICAL ASSISTANT VEHICLE AND INTERFACE," filed Apr. 28, 2020. The U.S. Provisional Patent Application 63/016,801 is incorporated herein by reference.

BACKGROUND

Embodiments of the invention described in this specification relate generally to robotic and automated devices, and more particularly, to a robotic medical assistant vehicle and interface (R-MAVI).

Public health crises like the unprecedented COVID-19 pandemic overwhelm the healthcare system. As hospitals get overflowed with patients, both corona virus victims, as well as other types of care seekers, suffer the consequences of an extreme lack of resources and limited personnel. Additionally, health care workers, particularly medical assistants, put themselves at risk and use their precious time on simple tasks that could be easily automated.

The emphasis is not on reducing exposure risk or streamlining the patient's assessment. There is no integration with other platforms. As for human personal assistants, they perform these tasks themselves, greatly increasing human interactions around medical facilities.

Therefore, what is needed is a way to help contain viruses by reducing human interaction without reducing medical safety, efficient reception, transportation, and initial assessment of a patient.

BRIEF DESCRIPTION

A novel robotic medical assistant vehicle and interface (R-MAVI) that provides automated medical assistance in ways that help contain viruses by reducing human interaction and a medical assistance process for operating a robotic medical assistant vehicle and interface (R-MAVI) are disclosed. In some embodiments, the R-MAVI combines robotics with medicine to achieve safe and efficient reception, transportation, and initial assessment of a patient.

In some embodiments, the R-MAVI comprises a plurality of drive motors, a plurality of wheels to move the R-MAVI between locations, a base plate, batteries, a micro-controller and breadboard to carry out logic instruction sets for engaging patients and automatically navigating/driving to different locations, a line sensor configured to detect a line pathway to follow while driving between locations, a pair of side rail arms, a plurality of ultrasonic sensors, a rotating tablet mount, a tablet computing device with a mobile app and interface to provide patient interaction and data input, a vitals measurement system and vital sign monitor, an EKG sensor that measures electrical activity of the heart of a patient, an internal temperature sensor that measures internal body temperature of the patient, a blood pressure testing machine, a wireless communication module, smart cables, transistors, and resistors for internal wiring, a seat box the encloses one or more electrical components, a seat on which the patient may be seated, and a weight scale under the seat which detects the patient's weight when seated.

In some embodiments, the R-MAVI is sterilized and sanitized after usage by way of an external sanitizing tunnel system that is configured to disinfect and clean the R-MAVI when the R-MAVI is present on a platform surface within the external sanitizing tunnel system.

The preceding Summary is intended to serve as a brief introduction to some embodiments of the invention. It is not meant to be an introduction or overview of all inventive subject matter disclosed in this specification. The Detailed Description that follows and the Drawings that are referred to in the Detailed Description will further describe the embodiments described in the Summary as well as other embodiments. Accordingly, to understand all the embodiments described by this document, a full review of the Summary, Detailed Description, and Drawings is needed. Moreover, the claimed subject matters are not to be limited by the illustrative details in the Summary, Detailed Description, and Drawings, but rather are to be defined by the appended claims, because the claimed subject matter can be embodied in other specific forms without departing from the spirit of the subject matter.

BRIEF DESCRIPTION OF THE DRAWINGS

Having described the invention in general terms, reference is now made to the accompanying drawings, which are not necessarily drawn to scale, and wherein.

DETAILED DESCRIPTION

In the following detailed description of the invention, numerous details, examples, and embodiments of the invention are described. However, it will be clear and apparent to one skilled in the art that the invention is not limited to the embodiments set forth and that the invention can be adapted for any of several applications. Also, in the present specification, terms such as 'approximate,' 'approximately,' 'about,' etc., as used herein indicate a deviation of within +/−10%. Relationships between the various elements of the disclosed robotic medical assistant vehicle and interface as described herein are presented as illustrative examples only, and not intended to limit the scope or nature of the relationships between the various elements.

Some embodiments include a robotic medical assistant vehicle and interface (R-MAVI) that provides automated medical assistance and human medical assistance in ways that help contain viruses by reducing human interaction and a medical assistance process for operating a robotic medical assistant vehicle and interface (R-MAVI). In some embodiments, the R-MAVI combines robotics with medicine to achieve safe and efficient reception, transportation, and initial assessment of a patient.

In some embodiments, the R-MAVI comprises a plurality of drive motors, a plurality of wheels to move the R-MAVI between locations, a base plate, batteries, a micro-controller and breadboard to carry out logic instruction sets for engaging patients and automatically navigating/driving to different locations, a line sensor configured to detect a line pathway to follow while driving between locations, a pair of side rail arms, a plurality of ultrasonic sensors, a rotating tablet mount, a tablet computing device with a mobile app and interface to provide patient interaction and data input, a vitals measurement system and vital sign monitor, an EKG sensor that measures EKG for heart rate of the patient when the patient places a finger on the EKG sensor, an internal temperature sensor that measures internal body temperature of the patient, a blood pressure testing machine, a wireless communication module, smart cables, transistors, and resistors for internal wiring, a seat box the encloses one or more electrical components, a seat on which the patient may be seated, and a weight scale under the seat which detects the patient's weight when seated. In some embodiments, the R-MAVI further comprises a COVID-19 test kit with a bio-sample swab device that captures a saliva sample of the patient when the bio-sample swab device touches the back of the throat and nostrils of the patient. In some embodiments, the R-MAVI further comprises a 360 degree camera and sensor system. In some embodiments, the R-MAVI is sterilized and sanitized after usage by way of an external sanitizing tunnel system that is configured to disinfect and clean the R-MAVI when the R-MAVI is present on a platform surface within the external sanitizing tunnel system.

As stated above, public health crises like the unprecedented COVID-19 pandemic overwhelm the healthcare system. As hospitals get overflowed with patients, both corona virus victims, as well as other types of care seekers, suffer the consequences of an extreme lack of resources and limited personnel. Additionally, health care workers, particularly medical assistants, put themselves at risk and use their precious time on simple tasks that could be easily automated. Embodiments of the robotic medical assistant vehicle and interface described in this specification solve such problems by reducing unnecessary human interaction through automating the reception and in-house transportation of patients while monitoring vitals and allowing for medical form filing in a safe, smart, sanitary, and automated way.

In some embodiments, the robotic medical assistant vehicle and interface is fully integrated with medical software and systems. Examples of the medical software and systems which the robotic medical assistant vehicle and interface is integrated include, without limitation, EPIC, systems that store medical and patient data, where the robotic medical assistant vehicle and interface is capable of automatically uploading individual patient information. By understanding a patient's symptoms, this medical assistant can make an undefined preliminary diagnosis of the patient. Ultimately reducing the risk of doctors and other healthcare workers from contracting viruses like COVID-19. This medical assistant gives more hands to help with medical overflows by doing simple tasks that are time-consuming. Overall, the robotic medical assistant vehicle and interface saves valuable time for health care workers and can also improve the patient and work flow of any medical institution during both normal and unusual times.

Embodiments of the robotic medical assistant vehicle and interface described in this specification differ from and improve upon currently existing options. In particular, some universities and medical facilities have experimented with automated wheelchairs that allow for patient accessibility. However, these automated wheelchairs are not designed to perform a series of defined essential tasks, such as receiving, transporting and assessing a patient's health while minimizing human contact. In contrast, the robotic medical assistant vehicle and interface of the present disclosure is specifically capable of performing any such series of defined essential medical tasks, including tasks for receiving patients, transporting patients, and assessing patient health—all while minimizing human contact and human-to-human exposure.

In addition, some embodiments of the robotic medical assistant vehicle and interface improve upon the currently existing options which are not designed to reduce human-to-human exposure and/or contact or to work efficiently and automatically under times of medical patient overflow, such as may be the case when pandemics are declared (e.g., for the novel corona virus and the related overflow of patients seeking medical treatments or testing). Typically, the existing options are limited to only one aspect of automated assistance, such as transportation of patients (e.g., automated wheelchairs). However, the improvements afforded by the robotic medical assistant vehicle and interface of the present disclosure helps contain viruses by reducing human interaction, such as face-to-face patient intake, and human-conducted preliminary patient screening, or obtaining patient bio-samples. By combining robotics with medicine, the robotic medical assistant vehicle and interface of the present specification achieves the safest and most efficient reception, transportation, and initial assessment of a patient. Further details of the robotic medical assistant vehicle and interface are described below, which illuminates several manners in which the robotic medical assistant vehicle and interface achieves the safety level and efficiency level in the reception, transportation, and initial screening/assessment of patients.

The robotic medical assistant vehicle and interface of the present disclosure may be comprised of the following elements. This list of possible constituent elements is intended to be exemplary only and it is not intended that this list be used to limit the robotic medical assistant vehicle and interface of the present application to just these elements. Persons having ordinary skill in the art relevant to the present disclosure may understand there to be equivalent elements that may be substituted within the present disclosure without changing the essential function or operation of the robotic medical assistant vehicle and interface.

1. A base plate. In some embodiments, the base plate is an aluminum base plate. In some embodiments, the base plate is in the shape of a square. In a preferred embodiment, the base plate has dimensions of two feet by two feet. The base plate dimensions are preferred dimensions, not absolute dimensions, since the robotic medical assistant vehicle and interface can be built in different sizes or constructed according to different form factors.

2. A plurality of drive motors. In some embodiments, the plurality of drive motors comprise direct current (DC) motors capable of powering the drive-train components and a patient seated on the robotic medical assistant vehicle and interface. In some embodiments, the plurality of drive motors comprise four DC motors.

3. Four wheels to move the robotic medical assistant vehicle and interface. In some embodiments, the wheels are all terrain wheels. In some embodiments, the wheels have diameters of at least ten inches. In some embodiments, the wheels have diameters of at least ten inches and up to twenty-five inches. In some embodiments, two front wheels have shorter diameters than the diameters of the two back wheels of the robotic medical assistant vehicle and interface. In some embodiments, the two front wheels have diameters of approximately ten inches and the two back wheels have diameters of approximately twenty-five inches.

4. Two rechargeable lithium-ion batteries of between 12V and 36V or whatever output is needed to power the motors, sensors, computers, and tablet.

5. At least one micro-controller powerful enough to function as the central brain for all the electrical components. In some embodiments, the micro-controller comprises a plurality of sensor and device interface pins that receive sensor and device data readings for processing from various sensors and/or devices. In some embodiments, the micro-controller is a micro-computer with at least one processing unit. In some embodiments, the micro-controller is a computing device with at least one processing unit comprising multiple cores.

6. At least one breadboard capable of gauging electrical output to the electrical components.

7. A seat capable of supporting a human subject in a seated position. In some embodiments, the seat is an ergonomic seat with a back support. In some embodiments, the seat is large enough to support an adult human subject and secure enough to securely support a young child human subject. In this way, most regular-sized patients can be seated on the seat of the robotic medical assistant vehicle and interface.

8. A protective casing. In some embodiments, the protective casing comprises a hood and isolation tarp. In some embodiments, the hood and isolation tarp is made of a lightweight translucent material. In some embodiments, the lightweight translucent material comprises acrylic.

9. Two side arm rails ("side arms") large enough to serve as armrests, protect the drive motors, and house all the sensors. In some embodiments, the side arms are made of aluminum. In some embodiments, the side arms are mounted on a hinge for easy access of components. In some embodiments, each side arm is prefabricated from a lower side arm component and an upper side arm component.

10. One or more smart electrical cable(s) of sufficient length to connect the motors, the sensors, and the other electrical components of the robotic medical assistant vehicle and interface.

11. At least one line following sensor (or "line sensor") for navigation.

12. A plurality of ultrasonic sensors for navigation. In some embodiments, the plurality of ultrasonic sensors comprise two front ultrasonic sensors and two rear ultrasonic sensors. In some embodiments, the two front ultrasonic sensors detect distance to objects in front of the robotic medical assistant vehicle and interface when the robotic medical assistant vehicle and interface is moving forward. In some embodiments, the two rear ultrasonic sensors detect distance to objects behind the robotic medical assistant vehicle and interface when the robotic medical assistant vehicle and interface is moving backward.

13. An attachable mount to which a tablet computing device can be mounted to interface with the robotic medical assistant vehicle and interface. In some embodiments, the attachable mount comprises a rotating tablet mount to hold the tablet computing device interface. In some embodiments, the rotating tablet mount comprises a plurality of mount lockable tablet rotation orientations. In some embodiments, the plurality of mount lockable tablet rotation orientations comprise a mount lockable portrait orientation and a mount lockable landscape orientation.

14. A vital sign monitor (or "vitals monitor") capable of monitoring body temperature, heart rate, blood pressure, and oxygen saturation via sensors, medical devices, and other medical machines.

15. A weight scale attachable to the seat.

16. A wireless communication module that allows remote operation of the robotic medical assistant vehicle and interface.

17. Transistors to amplify or switch electrical signals.

18. Resistors to gauge power to each component.

19. A tablet computing device and mobile app that provides a tablet interface for interacting with the robotic medical assistant vehicle and interface and viewing visually output data, graphics, imagery, and information related to patient health (e.g., vitals), patient privacy, patient payments, and patient authorizations.

20. A seat box that supports the seat at an elevation above the base plate. In some embodiments, the seat box comprises a hollow box positioned atop the base plate with the seat disposed atop the seat box. In some embodiments, the seat box is made of aluminum.

21. A separate sanitizing tunnel system. In some embodiments, the sanitizing tunnel system comprises a disinfectant tunnel, ramps that allow the robotic medical assistant vehicle to drive up to a disinfectant platform surface of the disinfectant tunnel to commence cleaning and to drive down from the disinfectant platform surface and out of the disinfectant tunnel after cleaning is completed, a disinfectant tank that is configured to hold a disinfectant spray solution, piping and spray nozzles, and a pump to pump the disinfectant spray solution up from the disinfectant tank through the piping and out of the spray nozzles and onto the robotic medical assistant vehicle when the robotic medical assistant vehicle is positioned within the disinfectant tunnel. In some embodiments, the sanitizing tunnel system further comprises batteries to provide power and a micro-controller to provide logic processing and automated disinfecting of the robotic medical assistant vehicle. The separate sanitizing tunnel system is described further below, by reference to FIG. 6.

The various elements of the robotic medical assistant vehicle and interface of the present disclosure may be related in the following exemplary fashion. It is not intended to limit the scope or nature of the relationships between the various elements and the following examples are presented as illustrative examples only. The base plate (#1, above) serves as the base platform upon which the drive motors (#2, above) and the wheels (#3, above) are mounted to create a moveable drive-train. The batteries (#4, above) are mounted on the base plate to provide power. The micro-controller (#5, above) and the breadboard (#6, above) are attached at the back half portion of the base (#1, above). The line sensor (#11, above) is mounted on the underside of the base plate nearby the drive-train. The side rails (#9, above) are placed on each side of the R-MAVI. Ultrasonic sensors (#12, above) are placed within their designated spots within the side rails. The rotating tablet mount (#13, above) is attached to a pivoting bar and the tablet interface (#19, above) attaches to the mount. The vital sign monitor (#14, above) is placed within the storage compartment(s) of a side rail. The wireless communication module (#15, above) is embedded in a back support connected to the seat. The smart cables (#10, above) are cut to the right lengths and wired into appropriate parts, utilizing transistors (#17, above) and resistors (#18, above) to wire the vitals monitor, the tablet, line sensor, ultrasonic sensor, motors, and wireless transmitter to the breadboard so that they can be powered and correspondingly connected to the micro-controller. The seat box (#20, above) is hollow and includes an open bottom and is placed on top of many of the electrical components on the base plate. The seat and support (#7, above) are placed on top of the seat box. The weight scale (#16, above) is placed between seat and the seat box. Externally, the sanitizing tunnel system (#21, above) is designed to sanitize the R-MAVI when positioned in or when driving through the tunnel.

The robotic medical assistant vehicle and interface of the present disclosure generally works by providing an isolated, single point of medical testing that would normally be done by a health care worker. At a medical facility, the robotic medical assistant vehicle and interface would be programmed to operate autonomously. In addition, the robotic medical assistant vehicle and interface can be configured for remote operation, by human interaction at a command station that is wirelessly and communicably connected to the robotic medical assistant vehicle and interface to take particular command orders from the human at the command station. During automated operation (or via remote command), the robotic medical assistant vehicle and interface would receive patients at medical facilities and transport them to where they need to be. The adjustable chair of the robotic medical assistant vehicle and interface allows for comfort of the patient during transit and a removable isolation hood allows for cleansing and sanitation. The attachable tablet interface (referred to as the "R-MAVI Sidekick") is used as a console to allow the patient to input information to be later shared with a doctor or other medical professional. The patient would use the tablet interface to enter their personal details on the screen, such as name, medical number, contact information, doctor email, and other important information as needed. In addition, the interface would be used to describe other important information necessary for making a diagnosis. Examples of other important information which a patient may input include, without limitation, a reason for the patient's visit to the hospital/medical facility, the magnitude of pain the patient is suffering from, other possible conditions or symptoms of which should the doctor/medical professional should be aware, including pre-existing conditions of the patient, which are recorded in the system. The program would then request the patient to perform a self-completable medical check by using the various systems on the device. The attached vital sign monitor would them perform a series of medical examinations, such as body temperature, pulse rate, blood pressure, and oxygen saturation, making it as effortless as possible for the patient to follow. The integrated weight sensor would also take a patient's weight into consideration for the pre-diagnosis. An optional Corona Virus Swab test would facilitate testing for the virus. The software on the tablet interface compiles all the information into a report that is sent to a doctor or other medical professional. While all of this is happening, the radio control capabilities of the robotic medical assistant vehicle and interface allows it to be controlled remotely (e.g., via human interaction at a remote command station or other) to move a patient through the facility. After a patient has either been discharged or moved to a different area, the robotic medical assistant vehicle and interface may no longer be needed for this particular patient. In such case, the robotic medical assistant vehicle and interface would automatically return for patient intake/preliminary screening of other patients at the facility.

In some embodiments, the robotic medical assistant vehicle and interface includes controls for the medical components comprising an EKG (when a finger of the patient is placed on the sensor, the robotic medical assistant vehicle and interface will display a graph, such as offered by way of the KardiaMobile App), a weight sensor (when the patient stands on the scale, the weight sensor will read a measurement), an internal temperature sensor (by pushing a button, the temperature sensor/thermometer will measure and record the patient's internal body temperature), a blood pressure sensor (the patient puts an arm band around patient's arm and uses equipment to record blood pressure), a heart rate sensor (patients puts a finger on the sensor and waits till a value appears on the monitor), and an oxygen saturation probe (or pulse oximeter probe) that on the top of the finger measures the oxygen saturation of a patient.

To make the robotic medical assistant vehicle and interface of the present disclosure, one would combine all the parts in a particular arrangement. Specifically, the robotic medical assistant vehicle and interface includes an ergonomic seat and support system, a hood and isolation equipment system, a brain and control system, motors, a battery and charging system, a teleop and autonomous operational system, an interactive graphic user interface system, a 360 degree camera and sensor system, a COVID-19 test kit and vital measurement system, and a separate standalone sanitizing tunnel system. Reinforcements and support structures are added to maintain the structural stability and integrity of the robotic medical assistant vehicle and interface during various operating conditions and transient situations. Certain different types of testing devices could be added for enhanced testing capabilities of the robotic medical assistant vehicle and interface.

To use the robotic medical assistant vehicle and interface of the present disclosure, a patient would sit down on the chair of the device. The robotic medical assistant vehicle and interface includes a button, such that a press of the button brings down the hood. The patient may use the tablet interface to input information, answer a questionnaire, and review/follow instructions to take their vitals. The program compiles a preliminary unofficial diagnosis and sends all the raw data directly to a doctor. During a time of pandemic, an additional sanitation tarp could be attached to the robotic medical assistant vehicle and interface and it could be remotely operated to minimize human contact and allow for safe, sanitary transportation within a medical facility.

Figure 1:
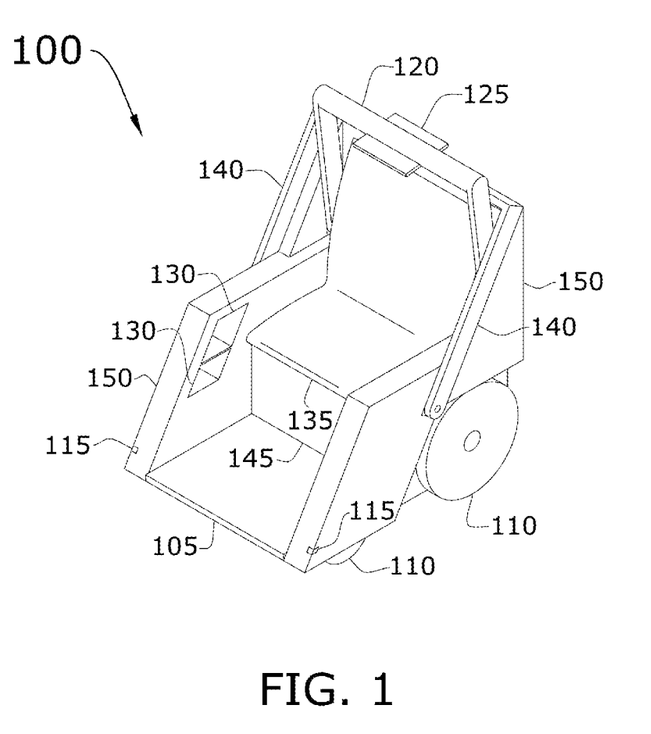
FIG. 1 conceptually illustrates a perspective view of a robotic medical assistant vehicle and interface (R-MAVI), shown open, in some embodiments.

By way of example, FIG. 1 conceptually illustrates a perspective view of a robotic medical assistant vehicle and interface (R-MAVI) in an open configuration 100. As shown in this figure, the R-MAVI includes several components. Specifically, the R-MAVI comprises a base plate 105, a plurality of wheels 110 to move the R-MAVI, a plurality of ultrasonic sensors 115 for navigation, a pivoting arm 120, a tablet computing device 125 that provides an interface for a patient or user of the R-MAVI, a plurality of storage compartments 130, a seat 135, a rotating encasing arm 140, a seat box 145, and a plurality of side arms 150 comprising two lower side arms and two upper side arms. In some embodiments, a prefabricated single side arm 150 comprising one lower side arm and one upper side arm is utilized along each of two opposing sides in the construction of the R-MAVI. In some embodiments, the side arms are made of aluminum with edges that act as rails which are big enough to serve as armrests. The side arm rails also protect drive motors (described below, by reference to FIG. 4) and house the ultrasonic sensors 115 near the front of the R-MAVI. Although not shown in this figure, the R-MAVI of some embodiments houses at least four ultrasonic sensors—two ultrasonic sensors housed in the lower front edges of the side arm rails (as shown in this figure), and two more ultrasonic housed near the back of the R-MAVI (for navigation during backward movement).

In a preferred embodiment, the base plate 105 is an aluminum base plate that has dimensions of two feet by two feet. In some other embodiments, the dimensions of the base plate are scaled upward or downward according to functional requirements of the robotic medical assistant vehicle and interface. For instance, a smaller robotic medical assistant vehicle and interface designed for children may feature a base plate of dimensions 1.5×1.5 feet.

In some embodiments, the plurality of wheels 110 comprise four wheels. In some embodiments, the wheels are all terrain wheels. In some embodiments, the wheels have diameters of at least ten inches. In some embodiments, the wheels have diameters of at least ten inches and up to twenty-five inches. In some embodiments, two front wheels have shorter diameters than the diameters of the two back wheels of the robotic medical assistant vehicle and interface. In some embodiments, the two front wheels have diameters of approximately ten inches and the two back wheels have diameters of approximately twenty-five inches. An example of an R-MAVI with two front wheels having shorter diameters than the diameters of two back wheels is described below, by reference to FIG. 4.

In some embodiments, the plurality of ultrasonic sensors 115 comprise two front ultrasonic sensors and two rear ultrasonic sensors. In some embodiments, the two front ultrasonic sensors detect distance to objects in front of the R-MAVI for navigation when the R-MAVI is moving forward. In some embodiments, the two rear ultrasonic sensors detect distance to objects behind the R-MAVI for navigation when the R-MAVI is moving backward.

Functionally, the R-MAVI shown in this figure is presented in the open configuration 100 with the rotating encasing arm 140 and the pivoting arm 120 positioned up above the seat 135. The tablet computing device 125 is attached to a front bar of the pivoting arm 120. Therefore, the tablet computing device 125 is also positioned up above the seat 135 in the open configuration 100. Thus, when the R-MAVI is in the open configuration 100, a patient is able to be seated on the seat 135 of the R-MAVI. After being seated, the pivoting arm 120 is lowered, which allows the patient to interface with the R-MAVI. Specifically, since the tablet computing device 125 is attached to the bar of the pivoting arm 120, the tablet 125 is re-positioned directly in front of the seated patient when the pivoting arm 120 is lowered to a resting position along a top edge of each of the two lower side arms 150. This changes the operational configuration of the R-MAVI from the open configuration 100 to a closed bar down configuration, which is described next, by reference to FIG. 2.

Figure 2:
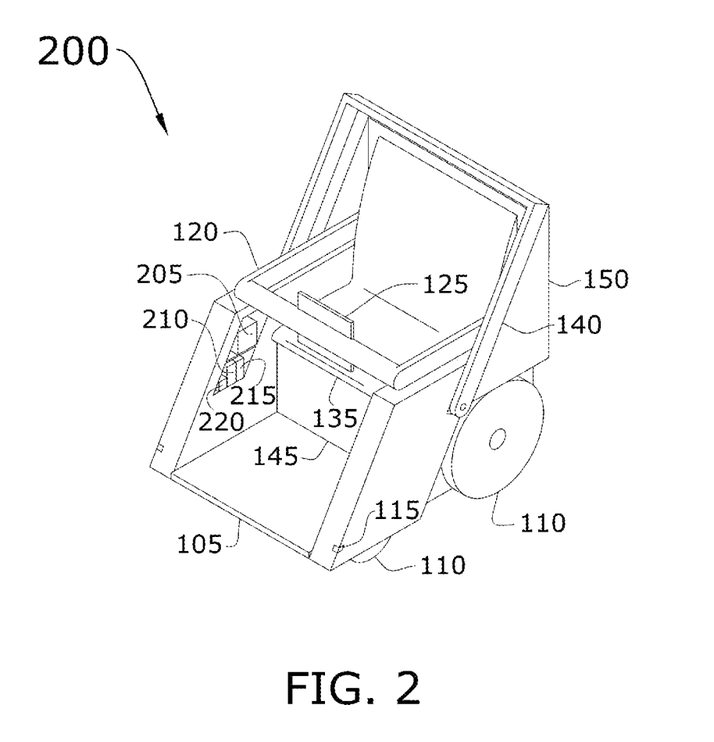
FIG. 2 conceptually illustrates the R-MAVI, shown with bar down, in some embodiments.

Specifically, FIG. 2 conceptually illustrates the R-MAVI in a closed bar down configuration 200 with the pivoting arm 120 lowered to the resting position along the top edges of the lower side arms 150. As shown in this figure, the R-MAVI further includes medical sensors 205, an electrocardiogram 210, a portable blood pressure machine 215, and a temperature sensor 220 in the plurality of storage compartments 130. The medical sensors 205, for example, may allow the R-MAVI to monitor oxygen saturation of a patient (via a pulse oximeter probe) or allow a patient to provide a bio-sample, such as may be needed to test for presence of infectious diseases (e.g., COVID-19), or detect other medical ailments or abnormalities of patients. The electrocardiogram 210 allows the R-MAVI to monitor heart rate of the patient. The portable blood pressure machine 215 allows the R-MAVI to monitor blood pressure of the patient. The temperature sensor 220 allows the R-MAVI to monitor body temperature of the patient. Also shown in this figure, the pivoting arm 120 has been lowered down and the tablet computing device 125 is positioned in a directly accessible front location with respect to any patient who may have sat down on the seat 135.

Figure 3:
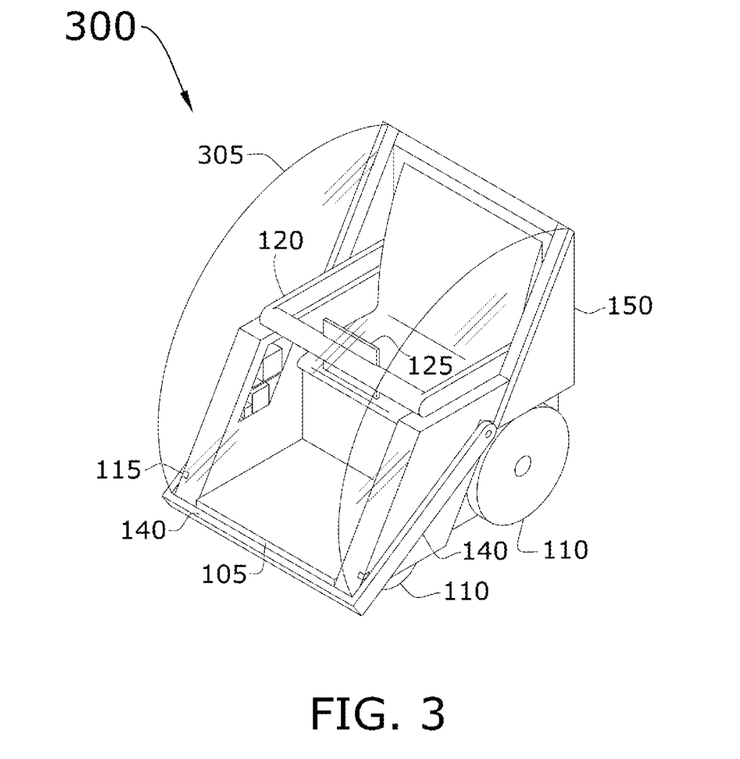
FIG. 3 conceptually illustrates the R-MAVI, shown with protective casing, in some embodiments.

Turning to another example of the R-MAVI, FIG. 3 conceptually illustrates the R-MAVI in a closed configuration 300 with a protective casing 305. In some embodiments, the protective casing 305 is made of translucent acrylic. In some embodiments, the protective casing 305 comprises a hood and isolation tarp that covers over the top of the patient seated in the seat 135 when the rotating encasing arm 140 is rotated down to a lowered position disposed approximately along the base plate 105.

Figure 4:
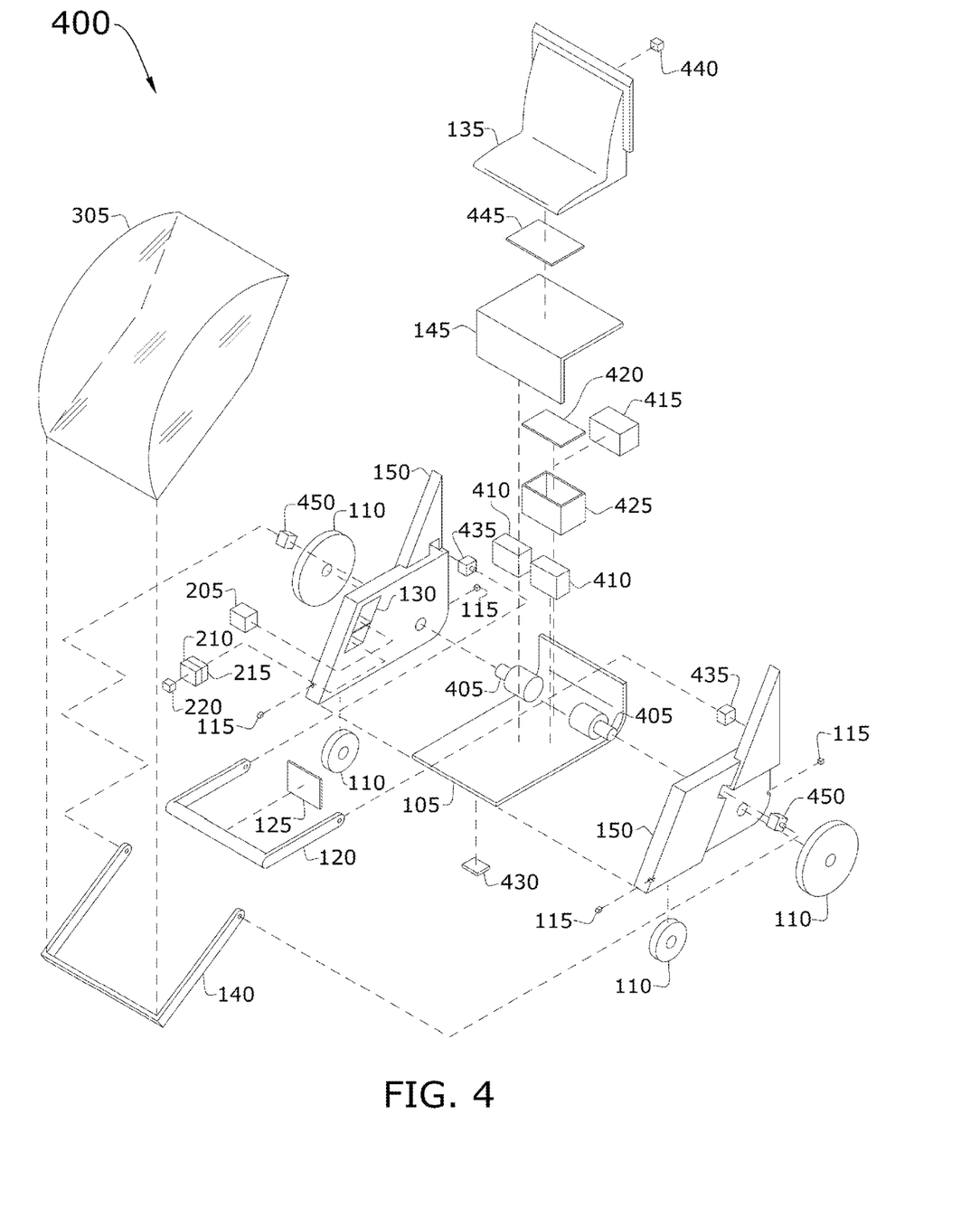
FIG. 4 conceptually illustrates an exploded view of the R-MAVI in some embodiments.

By way of example, FIG. 4 conceptually illustrates an exploded view of components of the R-MAVI 400. As shown in this figure, the R-MAVI 400 comprises the base plate 105, the plurality of wheels 110, the plurality of ultrasonic sensors 115, the pivoting arm 120, the tablet computing device 125, the plurality of storage compartments 130, the seat 135, the rotating encasing arm 140, the seat box 145, the plurality of side arm rails 150, the medical sensors 205, the electrocardiogram 210, the portable blood pressure machine 215, the temperature sensor 220, the protective casing 305, a plurality of drive motors 405, a plurality of batteries 410, a micro-controller and central electronics 415, an electronics housing lid 420, an electronics housing 425, a line sensor 430, a plurality of pivot arm motors 435, a wireless data communications module 440, a weight scale 445, and a plurality of rotating encasing arm motors 450. As shown, the two front wheels 110 have a shorter diameter than the two back wheels 110. The two front wheels are attached to the R-MAVI 400 from a partial enclosed location of the lower front portion of the side arms 150, which leaves a bottom part of the wheel exposed for surface contact. The two back wheels 110 are powered by the drive train of the R-MAVI 400 through direct connection to the drive motors 405. The drive motors 405 obtain power from the plurality of batteries 410. In some embodiments, the plurality of batteries 410 comprise lithium-ion batteries. When the R-MAVI 400 is assembled, the drive motors 405 are encapsulated inside and above the base plate 105. By contrast, the line sensor 430 is disposed along a bottom, external surface of the base plate 105, such that it is possible to detect a line for navigation of the R-MAVI 400.

The medical sensors 205, the electrocardiogram 210, the portable blood pressure machine 215, the temperature sensor 220 are installed in the plurality of storage compartments 130 and are either internally wired to the micro-controller and central electronics 415 or wirelessly connected to the wireless data communications module 440, which itself is communicably connected to the micro-controller and central electronics 415. (Hereinafter, internal hard wired data connections to the micro-controller and central electronics 415 and wireless data connections to the micro-controller and central electronics 415 by way of the wireless data communications module 440 are individually and collectively referred to as being "communicably connected to the micro-controller and central electronics 415".) Similarly, the weight scale 445 is communicably connected to the micro-controller and central electronics 415, such that when a patient sits in the seat 135, the weight scale 445 is able to determine the weight of the patient and provide the weight reading data to the micro-controller and central electronics 415.

The ultrasonic sensors 115 shown in this figure include two front ultrasonic sensors 115 and two back ultrasonic sensors 115. The ultrasonic sensors 115 are partial housed within the side arms 150 and partially exposed to detect distances to object in front of or in back of the R-MAVI to guide navigation during forward or backward movement. The ultrasonic sensors 115 are also communicably connected to the micro-controller and central electronics 415. The line sensor 430 noted above is also communicably connected to the micro-controller and central electronics 415 and sends line detection data to the micro-controller for realtime determinations of whether the R-MAVI is moving along an expected defined path (a "line"). When the line sensor 430 obtains line detection data that deviates from the expected path, the micro-controller provides realtime course changing instructions to the drive train and wheels to turn back toward the line.

The pivot arm 120 comprises two side pivot arms and a bar that connects the two side pivot arms together and to which the tablet computing device 125 is mounted. The two side pivot arms connect to the plurality of pivot arm motors 435. When powered by one or more of the plurality of batteries 410, the pivot arm motors 435 variably rotate the pivot arm 120 up to the open configuration 100 and down to the closed bar down configuration 200.

The rotating encasing arm 140 comprises two side encasing arms and a casing bar that connects the two side encasing arms together. The plurality of rotating encasing arm motors 450 connect to the two side encasing arms. When powered by one or more of the plurality of batteries 410, the plurality of rotating encasing arm motors 450 variably rotate the rotating encasing arm 140 up (to uncover the patient from the protective casing 305) and down (to cover the patient by the protective casing 305).

The seat 135 shown in this figure includes a back support, which also houses the wireless data communications module 440 and wiring that communicably connects the wireless data communications module 440 to the micro-controller and central electronics 415. The micro-controller and central electronics 415 is encapsulated within the electronics housing 425 and under the electronics housing lid 420, which are positioned atop the inner surface of the base plate 105, adjacent to the plurality of batteries 410, and nearby the plurality of drive motors 405. The seat box 145 covers and encloses the electronics housing 425 and lid 420, the plurality of drive motors 405, and the plurality of batteries 410. The seat 135 rests on top of the seat box 145, with the weight scale 445 sandwiched between them.

Figure 5:
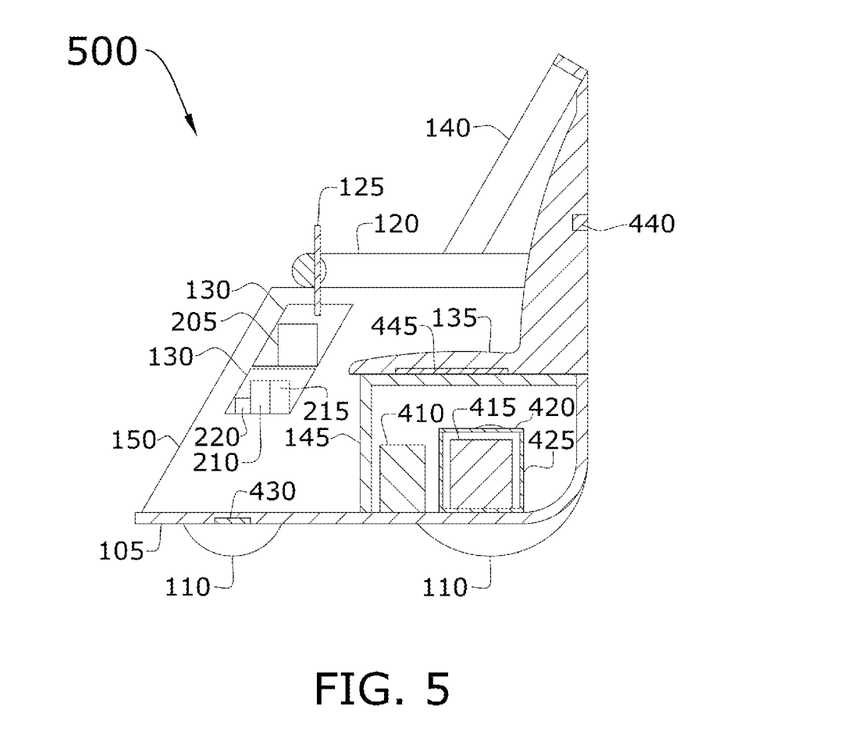
FIG. 5 conceptually illustrates a side section view of the R-MAVI in some embodiments.

In another view, FIG. 5 conceptually illustrates a side section view of the R-MAVI 500 which exhibits positioning and layout of many of the encapsulated components of the R-MAVI 400 described above, by reference to FIG. 4. As shown in this figure, the R-MAVI 500 is in the closed bar down configuration 200 with the pivoting arm 120 lowered to a resting position. The tablet computing device 125, which provides the interface for the user or patient, is mounted to the pivot bar of the pivoting arm 120. This position is directly in front of the patient who may be seated in the seat 135. The rotating encasing arm 140 is shown up and no protective casing 305 is shown here. The other components are shown largely in some connection to the base plate 105, which serves as a platform on which these other components are assembled. Specifically, the wheels are shown extending under the base plate 105 to make surface contact with a flat surface (the "ground"). The line sensor 430 is shown flush mounted along an external bottom surface of the base plate 105 and between the two front wheels 110. This positioning exposes the line sensor 430 to any line that is visible on the ground (or lack of line if not visible on the ground).

Above the base plate 105 is a side rail arm 150 (only one of two are shown from the side section view in this figure). The pivoting arm 120 rests along the top rail/edge of the side arm 150. Within the side rail arm 150 are the plurality of storage compartments 130 with the medical sensors 205 (such as, without limitation, a pulse oximeter probe to test oxygen saturation of a patient, a Corona virus swab, etc.), the electrocardiogram 210, the portable blood pressure machine 215, and the temperature sensor 220.

Above the base plate 105 is also the seat 135 with the wireless data communication module 440 embedded within a housing of a back support for the seat 135. Above the base plate 105 and enclosed within the base plate 105, the seat 135, and the side arms 150 is the weight scale 445, the seat box 145, a battery 410 from the plurality of batteries 410, the electronics housing 425 and lid 420, and the micro-controller and central electronics 415 which are enclosed within the electronics housing 425 and lid 420.

In some embodiments, a disinfectant cleaning tunnel is configured to sterilize a robotic medical assistant vehicle and interface (R-MAVI) after use. By way of example, FIG. 6 conceptually illustrates a disinfectant cleaning tunnel 600 that is configured to sterilize the R-MAVI after use. The disinfectant cleaning tunnel 600 is a sanitizing tunnel system that is separate from the R-MAVI. However, the disinfectant cleaning tunnel 600 is constructed with components that enable automated sterilization, disinfecting, and cleaning of the R-MAVI. As shown in this figure the disinfectant cleaning tunnel 600 comprises piping with spray nozzles 610, a disinfectant tank 620 that is configured to hold a disinfectant spray solution for cleaning the R-MAVI, a pump 630, batteries 640, a micro-controller 650, and a plurality of ramps 660.

Figure 6:
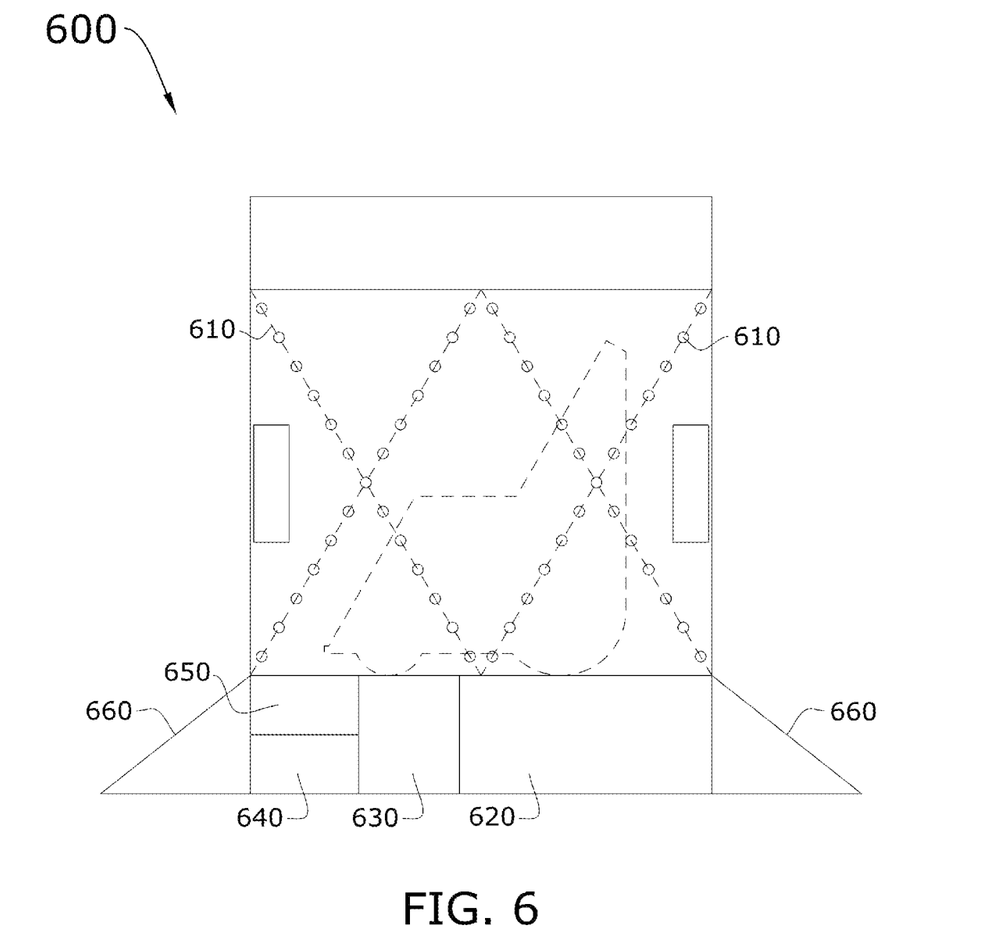
FIG. 6 conceptually illustrates a disinfectant cleaning tunnel configured to sterilize a robotic medical assistant vehicle and interface (R-MAVI) in some embodiments.

Operationally, the ramps 660 allow the R-MAVI to drive up to a disinfectant platform surface of the disinfectant cleaning tunnel 600 to commence cleaning and to drive down from the disinfectant platform surface and out of the disinfectant cleaning tunnel 600 after cleaning is completed. The disinfectant tank 620 is configured to hold a disinfectant spray solution and is large enough to hold disinfectant spray solution sufficient for one or more disinfecting cleanings of an R-MAVI. The piping and spray nozzles 610 are attached to an inner surface of the disinfectant cleaning tunnel 600 and placed in a distribution that optimizes spray coverage when cleaning an R-MAVI. The pump 630 is configured to pump the disinfectant spray solution up from the disinfectant tank 620 through the piping and out of the spray nozzles 610 and onto the R-MAVI when the R-MAVI is positioned on the disinfectant platform surface within the disinfectant cleaning tunnel 600. Additionally, the batteries 640 provide power for the disinfectant cleaning tunnel 600 and all electronic components, including the micro-controller 650, which configured to perform logic processing and automated disinfecting of the R-MAVI.

In some embodiments, the R-MAVI works by performing actions of a process for operating the R-MAVI (hereinafter referred to as the "R-MAVI medical assistance process"). By way of example, FIG. 7 conceptually illustrates the R-MAVI medical assistance process 700. As shown in this figure, the R-MAVI medical assistance process 700 renders functionality for the R-MAVI as a medical assistant (at 710), which can be as a human medical assistant (at 720) and/or an automated medical assistant (at 730). As human medial assistant (at 720), the R-MAVI medical assistance process 700 helps physicians with patient rooming (at 722). For example, the line sensor 430 allows the R-MAVI to accurately navigate along one or more defined paths ("lines") to take a patient to a particular medical location for examination by a physician or other clinician. The R-MAVI medical assistance process 700 includes operations in which the R-MAVI takes temperature, blood pressure, heart rate ("EKG"), oxygen saturation, and/or other vitals readings (at 724). This is done when the patient is seated on the seat 135 of the R-MAVI and by utilization of the medical devices and sensors stored in the storage compartments 130. The R-MAVI can also allow patients to self inject medicine as well as provide medication as directed by physicians and as permitted by law (at 726) as well as schedule patient appointments (at 728). For instance, the patient can interface with the tablet computing device 125 to schedule a follow-up or next appointment, and the wireless data communication module 440 can receive instructions from the physician or commands to provide medication or print prescription sheet, give a self-injection, etc. Thus, as a human medical assistant (at 720), the R-MAVI is capable of handling several medical needs.

Figure 7:
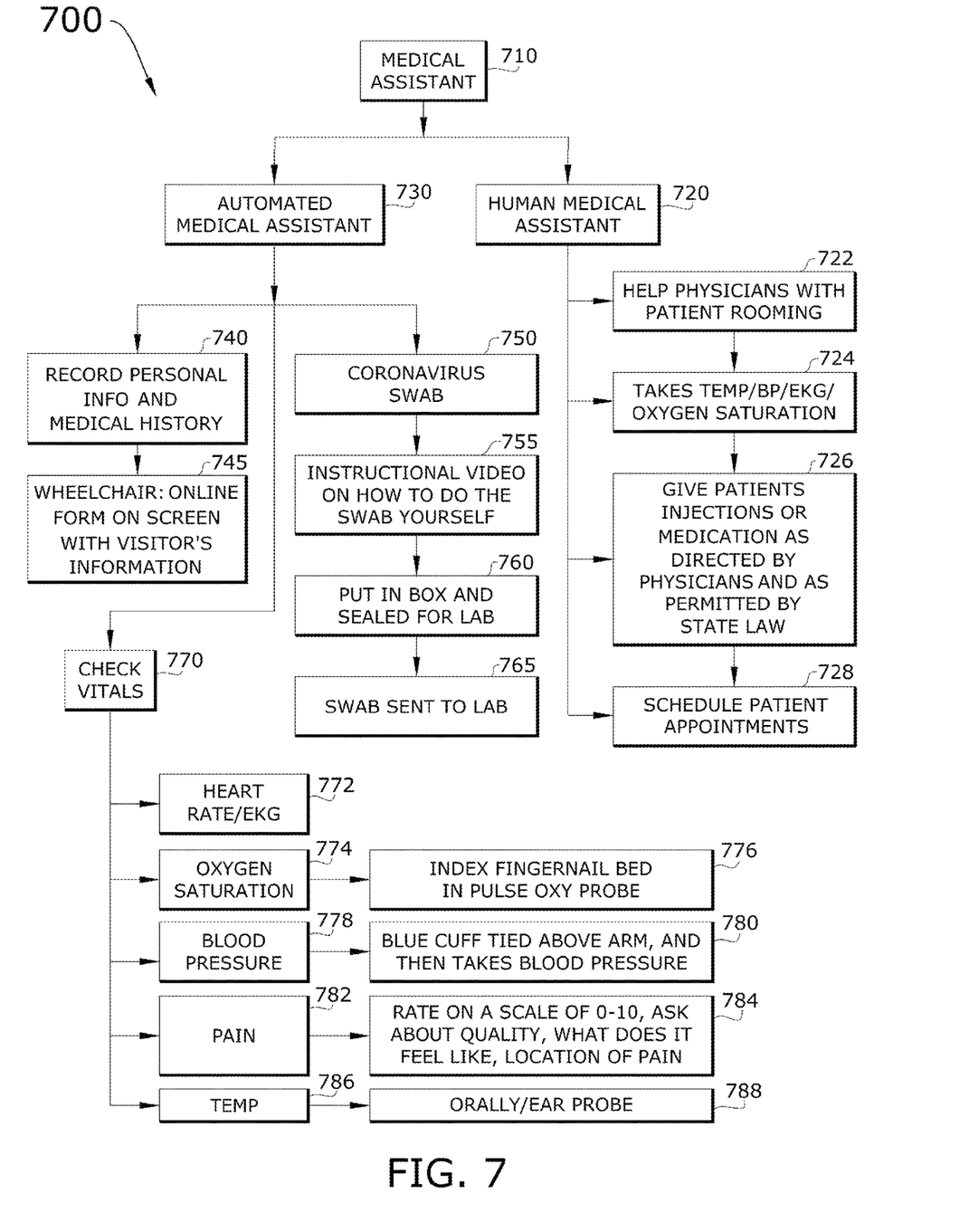
FIG. 7 conceptually illustrates a medical assistance process for operating a robotic medical assistant vehicle and interface (R-MAVI) in some embodiments.

The R-MAVI also works in many automated ways. This is shown in the R-MAVI medical assistance process 700 under the automated medical assistant (at 730), where the R-MAVI can record personal information about the patient (interactively via the tablet computing device 125) and medical history (by secure retrieval of patient medical record) and other such private medical data (at 740). For patients with wheelchair requirements, the R-MAVI medical assistance process 700 provides an online form on a touch-screen of the tablet with the visitor's information (at 745). In other automated medical assistant (at 730) functions, the R-MAVI can provide coronavirus swab (at 750) assistance including at least visually outputting instructional video(s) on how a patient can perform the swab on themselves (at 755) with the swab being put into a box of the R-MAVI and sealed for lab analysis (at 760), with the swab being delivered by the R-MAVI to a local onsite lab (at 765) via line sensor 430 following of a line that leads to a lab as instructed (received instruction through the wireless data communication module 440) or to a mail delivery service that delivers to the lab. Furthermore, the R-MAVI medical assistance process 700 includes operations for checking vitals (at 770). For vitals, the R-MAVI medical assistance process 700 checks heart rate/EKG (at 772) by way of the electrocardiogram 210. The R-MAVI medical assistance process 700 checks oxygen saturation (at 774) via medical sensors 205 that include a pulse oximeter probe in which the patient place an index finger (at 776). The R-MAVI medical assistance process 700 checks blood pressure (at 778) via the portable blood pressure machine 215 that includes a blue cuff which is tied above the arm of the patient, after which the R-MAVI takes the patient's blood pressure (at 780). The R-MAVI medical assistance process 700 checks a level of pain (at 782) which the patient rates and describes (at 784) via tablet interface that visually outputs a pain rating scale (e.g., pain scale from 0-10, or 0-100, or some other scale) from which the patient touches the tablet screen to indicate a pain level. The tablet computing device also visually outputs pain questions which the patient interactively answers (e.g., describe the quality of the pain, describe what the pain feels like, the location of the pain, etc.). The R-MAVI medical assistance process 700 also checks body temperature of the patient (at 786) via the temperature sensor 220 which can be an oral temperature sensor or an ear probe or other temperature sensor (at 788). In this way, the R-MAVI acts as an automated medical assistant (at 730).

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claims.

Also, many of the above-described features and applications are implemented as software processes that are specified as a set of instructions recorded on a computer readable storage medium (also referred to as computer readable medium or machine readable medium). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

In this specification, the terms "software", "application", "program", "interface", "app", and "mobile app" (referred to below as "software") are meant to include both firmware (residing in read-only memory) and/or installed applications stored in magnetic storage of a device. Furthermore, the software can be read into memory for processing by a processor, such as the processor of a mobile computing device or a mobile communications device, such as a smartphone, a hand-held computing device, or a tablet computing device (referred to simply as a "mobile device"), or the processor of a traditional computing device, such as a server computer, a desktop computer, or a laptop computer (referred to simply as a "computer"). Also, in some embodiments, multiple software inventions can be implemented as sub-parts of a larger program while remaining distinct software inventions. In some embodiments, multiple software inventions can also be implemented as separate programs. Finally, any combination of separate programs that together implement the medical assistance process 700 described above, by reference to FIG. 7, or the mobile interface app that runs on the tablet computing device 125, described above by reference to FIG. 1, is within the scope of the invention. In some embodiments, the software programs, when installed to operate on one or more electronic systems, define one or more specific machine implementations that perform the operations of the software programs for the R-MAVI, described above by reference to FIGS. 1-5, and/or the disinfectant cleaning tunnel, described above by reference to FIG. 6. Programmable processors, micro-controllers, and computers can be packaged or included in mobile devices or in custom hardware including the R-MAVI device and/or the disinfectant cleaning tunnel machine. The processes may be performed by programmable processors or micro-controllers and by one or more set of programmable logic circuitry. General and special purpose computing and storage devices can be interconnected through communication networks.

Figure 8:
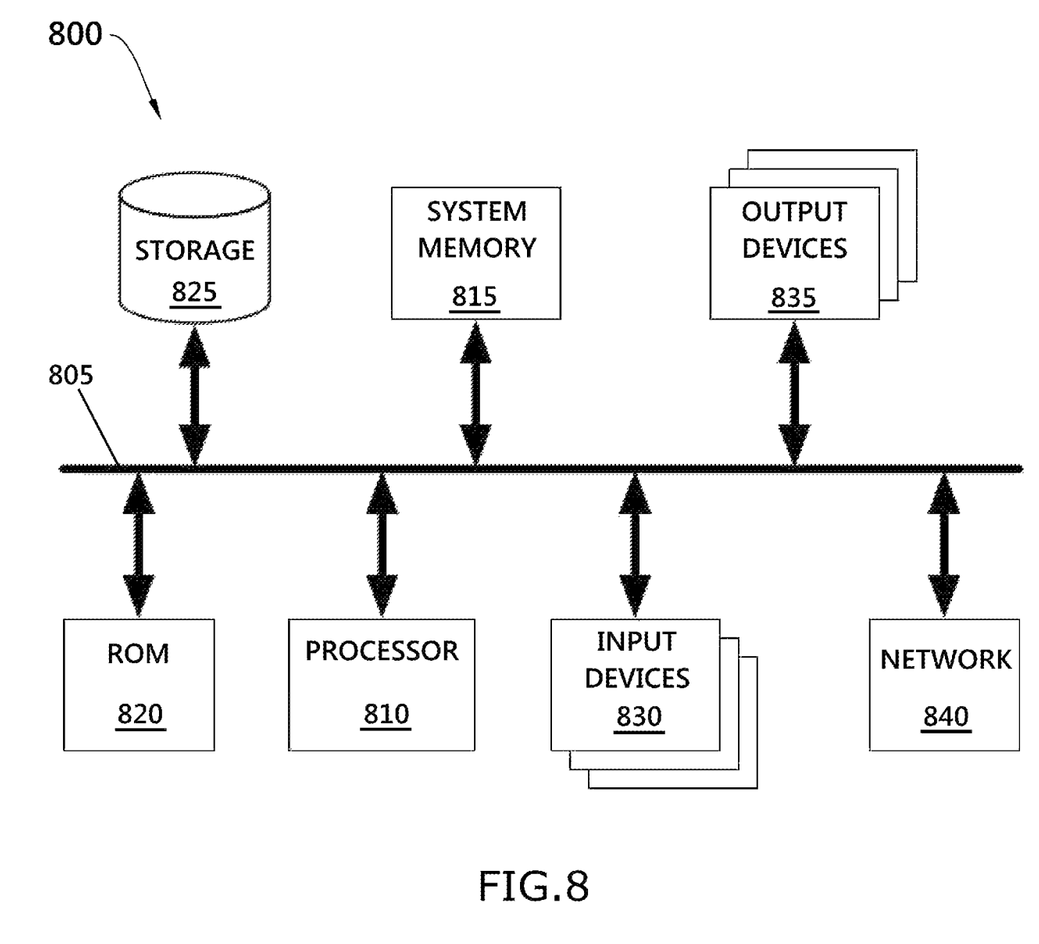
FIG. 8 conceptually illustrates an electronic system with which some embodiments of the invention are implemented.

FIG. 8 conceptually illustrates an electronic system 800 with which some embodiments of the invention are implemented. The electronic system 800 may be a computing device, such as a single board computer (SBC) or a micro-computer or micro-controller (e.g., Arduino, Raspberry Pi, etc.), a mobile device, such as a tablet computing device, a mobile phone (e.g., smartphone), another type of hand-held computing device such as a personal digital assistant (PDA), or any other sort of electronic device. Such an electronic system includes various types of computer readable media and interfaces for various other types of computer readable media. Electronic system 800 includes a bus 805, processing unit(s) 810, a system memory 815, a read-only memory 820, a permanent storage device 825, input devices 830, output devices 835, and a network 840.

The bus 805 collectively represents all system, peripheral, and chipset buses that communicatively connect the numerous internal devices of the electronic system 800. For instance, the bus 805 communicatively connects the processing unit(s) 810 with the read-only memory 820, the system memory 815, and the permanent storage device 825.

From these various memory units, the processing unit(s) 810 retrieves instructions to execute and data to process in order to execute the processes of the invention. The processing unit(s) may be a single processor or a multi-core processor in different embodiments. Examples of processing unit(s) 810 include, without limitation, a processor of a computing device or micro-controller, a processor with multiple cores of a computing device, a mobile processor of a tablet computing device, etc.

The read-only-memory (ROM) 820 stores static data and instructions that are needed by the processing unit(s) 810 and other modules of the electronic system 800. The permanent storage device 825, on the other hand, is a read-and-write memory device. This device is a non-volatile memory unit that stores instructions and data even when the electronic system 800 is off. Some embodiments of the R-MAVI use a mass-storage device (such as a magnetic or optical disk and its corresponding disk drive) as the permanent storage device 825.

Other embodiments use a removable storage device (such as a USB or flash drive) as the permanent storage device 825. Like the permanent storage device 825, the system memory 815 is a read-and-write memory device. However, unlike storage device 825, the system memory 815 is a volatile read-and-write memory, such as a random access memory. The system memory 815 stores some of the instructions and data that the processor needs at runtime. In some embodiments, implementations of the medical assistance process 700 are stored in the system memory 815, the permanent storage device 825, and/or the read-only memory 820. For example, the various memory units include instructions for the micro-controller (e.g., Arduino) of the R-MAVI to carry out operational instructions for the medical assistance process 700 as provided to the R-MAVI remotely through the wireless communication module 440 or otherwise. Similarly, these various memory units include mobile application implementations of the R-MAVI interface with instructions for the tablet computing device 125. From these memory units (whether it be the micro-controller of the R-MAVI, the micro-controller of the disinfectant cleaning tunnel, or a mobile processing unit of the tablet computing device 125 that provides the R-MAVI interface) the processing unit(s) 810 retrieves instructions to execute and data to process in order to execute the processes of some embodiments.

The bus 805 also connects to the input and output devices 830 and 835. The input devices enable the user to communicate information and select commands to the electronic system. The input devices 830 include sensors, such as the medical sensors 205, the ultrasonic sensors 115, and the temperature sensor 220, and/or devices, such as the electrocardiogram 210, the portable blood pressure machine 215, and other such devices and sensors. The input devices 830 may be hard-wire or wirelessly connected to sensor and device modules secured to a breadboard interface or connectors of a micro-controller (such as an Arduino single board computer (SBC) or other electronic system). The input devices 830 also may include alphanumeric keyboards and pointing devices (also called "cursor control devices"), which may be provided as physical hardware input devices or virtual input devices (e.g., keyboard displayed on touchscreen of the tablet interface of the R-MAVI). The output devices 835 display images generated by the electronic system 800, including patient readings (e.g., numerical, graphical, informational, etc.), textual information (e.g., instructions, summaries and details, follow-up information, etc.), and other such visual data. The output devices 835 include printers (e.g., printed receipts for co-payments, follow-up instructions, etc.) and display devices, such as liquid crystal displays (LCD), organic light emitting diode (OLED) displays, etc. Some embodiments include devices, such as the tablet computing device which provides an interface for the R-MAVI via a touchscreen, which functions as both an input device (receiving touch gesture input from a user, a patient, a medical professional, etc.) and as an output device (visually outputting information, such as medical readings of a patient, e.g., vitals tested and measured, then displayed on the tablet's touchscreen).

Finally, as shown in FIG. 8, bus 805 also couples electronic system 800 to a network 840 through a network adapter (not shown), which may support a hard-wired network connection (e.g., an Ethernet network connection), a wireless network connection (e.g., WiFi), or both a hard-wired and wireless network connection. In this manner, the computer can be a part of a network of computers (such as a local area network ("LAN"), a wide area network ("WAN"), or an intranet), or a network of networks (such as the Internet). Any or all components of electronic system 800 may be used in conjunction with the invention.

While the invention has been described with reference to numerous specific details, one of ordinary skill in the art will recognize that the invention can be embodied in other specific forms without departing from the spirit of the invention. For instance, FIG. 7 conceptually illustrates a medical assistance process for operating a robotic medical assistant vehicle and interface (R-MAVI) in which the specific operations of the process may not be performed in the exact order shown and described. Specific operations may not be performed in one continuous series of operations, and different specific operations may be performed in different embodiments of the R-MAVI. Furthermore, the process could be implemented using several sub-processes, or as part of a larger macro process. Thus, one of ordinary skill in the art would understand that the invention is not to be limited by the foregoing illustrative details, but rather is to be defined by the appended claims.

We claim:

1. A robotic medical assistant vehicle and interface (R-MAVI) comprising:
    a plurality of drive motors;
    a plurality of wheels configured to move the R-MAVI between locations, wherein the plurality of wheels comprise two front wheels with front wheel dimeters and two back wheels with back wheel diameters, wherein the front wheel diameters are shorter than the back wheel diameters;
    a base plate;

a micro-controller configured to early out logic instruction sets for engaging patients and automatically moving the R-MAVI to different locations;

a line sensor configured to detect a line pathway to follow for navigating the MAW while moving between locations;

a plurality of ultrasonic sensors that are configured to detect distance to objects in a path of the R-MAVI while moving;

a vitals measurement system and vital sign monitor;

an EKG sensor that is configured to measure EKG for heart rate of the patient when a finger of the patient is in contact with the EKG sensor;

an internal temperature sensor that is configured to measure internal body temperature of the patient;

a blood pressure testing machine configured to measure blood pressure of the patient;

an oxygen saturation probe configured to measure oxygen saturation of the patient;

a wireless communication module configured to receive instructions for operating and navigating the R-MAVI, said instructions for operating and navigating the R-MAVI transmitted from the wireless communication module to the micro-controller for realtime processing;

a pair of side rail arms;

a tablet computing device with a mobile app and interface configured to provide patient interaction and data input;

a tablet mount to which the tablet computing device is mounted;

a rotating pivot arm to which the tablet mount is mounted;

a plurality of pivot arm motors configured to rotate the rotating pivot arm between a raised orientation and a forward orientation;

a seat on which the patient may be seated;

a seat box that is positioned on the base plate and on which the seat is positioned, wherein the seat box encloses one or more electrical components of the R-MAVI;

a protective casing comprising a hood and isolation tarp;

a rotating encasing arm that is attached to the protective casing and is configured to rotate down to reveal the protective casing and to rotate up to a raised position that conceals the protective casing, wherein the rotating encasing arm is configured to pull the protective casing along a downward rotation path as the rotating encasing arm rotates down to a lowered position disposed along the base plate to encapsulate the rotating pivot arm, the tablet mount, the tablet computing device, the pair of side rails, the seat box, the seat, and the patient when the patient is seated on the seat;

a weight scale under the seat and above the seat box which detects the patient's weight when seated on the seat; and a plurality of batteries that provide power to the drive motors, the pivot arm motors, the micro-controller, the line sensor, the plurality of ultrasonic sensors, the vitals measurement system and vital sign monitor, the EKG sensor, the internal temperature sensor, the blood pressure testing machine, the oxygen saturation probe, the wireless communication module, and the weight scale.

2. The R-MAVI of claim 1 further comprising a COVID-19 test kit with a bio-sample swab device that is configured to capture a saliva sample of the patient when throat and nostrils of the patient contact the bio-sample swab device.

3. The R-MAVI of claim 1, wherein the batteries are lithium-ion batteries mounted to the base plate.

4. The R-MAVI of claim 1, wherein the two back wheels are connected to the drive motors.

5. The R-MAVI of claim 1, wherein the line sensor is mounted to an external surface of the base plate between the two front wheels.

6. The R-MAVI of claim 1, wherein the plurality of ultrasonic sensors comprise two front ultrasonic sensors and two back ultrasonic sensors.

7. The R-MAVI of claim 6, wherein the two front ultrasonic sensors are configured to detect distance in front of the R-MAVI as the R-MAVI is moving forward and the two back ultrasonic sensors are configured to detect distance behind the R-MAVI as the R-MAVI is moving backward.

8. The R-MAVI of claim 1, wherein the R-MAVI is configured to rest on a platform of an external sanitizing tunnel system to disinfect and clean the R-MAVI after use.

9. The R-MAVI of claim 1, wherein the protective casing is made of translucent acrylic.

* * * * *